United States Patent [19]

Darms et al.

[11] 4,200,724
[45] Apr. 29, 1980

[54] POLYMER CONTAINING IMIDYL GROUPS AND SILYL GROUPS

[75] Inventors: Roland Darms, Therwil; Siegfried Wyler, Dornach, both of Switzerland

[73] Assignee: Ciba-Geigy Corporation, Ardsley, N.Y.

[21] Appl. No.: 938,168

[22] Filed: Aug. 30, 1978

[30] Foreign Application Priority Data

Sep. 9, 1977 [CH] Switzerland .................... 11069/77

[51] Int. Cl.$^2$ ............................................. C08G 77/04
[52] U.S. Cl. .................................... 528/26; 427/387; 428/428; 528/27; 528/38; 556/419
[58] Field of Search ........................... 528/26, 27, 38; 260/448.8 R, 448.2 Q

[56] References Cited

U.S. PATENT DOCUMENTS

| | | | |
|---|---|---|---|
| 3,926,911 | 12/1975 | Greber et al. | 528/26 |
| 3,948,835 | 4/1976 | Greber et al. | 260/2 S |
| 3,950,308 | 4/1976 | Greber et al. | 528/26 |
| 3,966,531 | 6/1976 | Bargain | 156/329 |
| 4,088,670 | 5/1978 | Bargain et al. | 260/448.2 Q |

OTHER PUBLICATIONS

Lipinski, Defazet, 28, 207 (1974).
Hoersch, Kunstoffe, 55, 909 (1965).
Chemical Abstracts, 86, 139852y (1977).
Chemical Abstracts, 87, 109428t (1977).

*Primary Examiner*—Melvyn I. Marquis
*Attorney, Agent, or Firm*—Luther A. R. Hall

[57] ABSTRACT

The compounds according to the invention are polymers, containing imidyl groups and silyl groups, of the formula

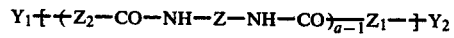

in which $Y_1$ and $Y_2$ are Si-organic radicals, a is an integer from 1 to 50 and Z, $Z_1$ and $Z_2$ independently of one another are each divalent organic radicals, but at least one of the radicals $Z_1$ and $Z_2$ is a group which contains an unsubstituted or substituted imidyl group.

The products according to the invention may be prepared, for example, by a multi-stage reaction of m-phenylenediamine, 5-dimethylmaleimidyl-isophthalic acid dichloride, 3,3'-4,4'-benzophenonetetracarboxylic acid dianhydride and γ-aminopropyl-di-n-propoxymethylsilane in solution.

The products are used as adhesion promoters, for example between inorganic solids and organic resins.

13 Claims, No Drawings

POLYMER CONTAINING IMIDYL GROUPS AND SILYL GROUPS

The present invention relates to novel polymers, containing imidyl groups and silyl groups, to a process for their preparation and to their use as adhesion promoters, for example between inorganic solids and organic resins, of for the preparation of crosslinked mouldings.

The literature discloses that various silanes, for example vinyltrichlorosilane, vinyl-tris-(2-methoxyethoxy)-silane and γ-aminopropyltriethoxysilane, may be used as adhesion promoters for various applications, for example for the production of glass fibre-reinforced plastics, for sealants, for lacquers and for adhesives [compare, for example, Defazet, 28, 207–211 (1974) and Kunststoffe, 55, 909–912 (1965)]. However, the properties of the products obtained using these known adhesion promoters in part leave something to be desired, especially in respect of water absorption, resistance to thermal oxidation and/or dielectric properties.

German Offenlegungsschrift No. 2,426,885 describes silicon-modified crosslinkable polyamide prepolymers and polyamidoacid prepolymers as polymeric base materials. In these prepolymers, crosslinking takes place via the two terminal silyl groups. Accordingly, the degree of crosslinking of these prepolymers is limited.

The present invention relates to novel polymers, containing imidyl groups and silyl groups, which on the one hand, when used as adhesion promoters, give products with improved properties, especially improved resistance to thermal oxidation, improved electrical properties and/or lower water absorption and, on the other hand, may be used to produce highly crosslinked polymeric mouldings.

The novel polymers, containing imidyl groups and silyl groups, correspond to the formula I $$Y_1 + (Z_2-CO-NH-Z-NH-CO)_{a-1} Z_1 + Y_2 \quad (I)$$

in which $Y_1$ and $Y_2$ independently of one another are a

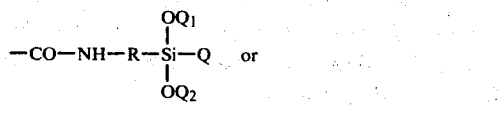

group, R is $-(CH_2)_x-$, 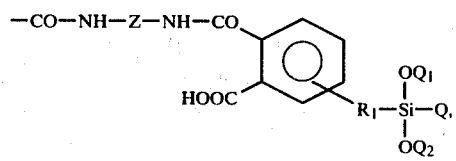 or

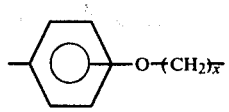

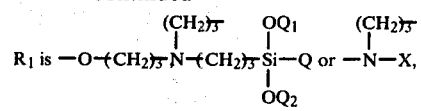

X is alkyl with 2–7 C atoms, cycloalkyl with 5–7 C atoms or benzyl, Q is methyl, phenyl or $-OQ_3$, $Q_1$, $Q_2$ and $Q_3$ independently of one another are alkyl with 1–6 C atoms or phenyl, x is an integer from 2 to 4, a is an integer from 1 to 50, the individual radicals Z independently of one another are an aliphatic radical with at least 2 C atoms, or a cycloaliphatic, araliphatic, carbocyclic-aromatic or heterocyclic-aromatic radical and $Z_1$ and the individual radicals $Z_2$ independently of one another are a

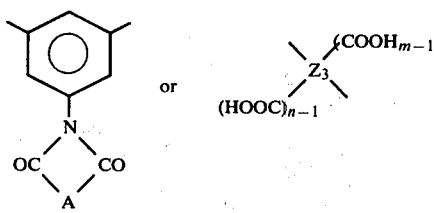

group, but at least one of $Z_1$ and $Z_2$ is a

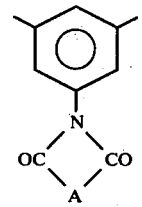

group, A is a radical

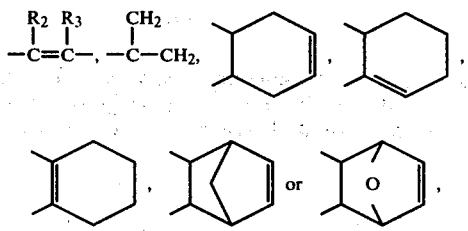

$R_2$ and $R_3$ independently of one another are hydrogen or methyl, the individual values m and n independently of one another are 1 or 2 and the individual radicals $Z_3$ independently of one another are an aliphatic radical with at least 2 C atoms, or a cycloaliphatic, carbocyclic-aromatic or heterocyclic-aromatic radical, in which the carboxamide and carboxyl groups are bonded to different C atoms and carboxyl groups bonded to cyclic radicals $Z_3$ are each in the ortho-position to a carboxamide group.

The invention further relates to the derivatives which have been cyclised to the corresponding imides.

The polymers of the formula I and the corresponding cyclised derivatives can be prepared by a method wherein, if a is 1, a compound of the formula II

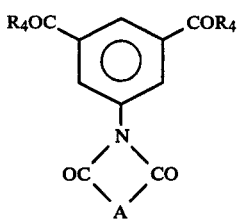
(II), and, if a>1, a compound of the formula III

Z$_4$—CO—NH—Z—NH—CO+Z$_2$—CO—N-
H—Z—NH—CO$\overline{)_{a_1-1}}$Z$_5$ (III)

in which Z$_4$ and Z$_5$ independently of one another are a

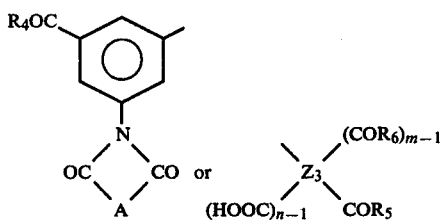

group, is reacted with an essentially stoichiometric amount of a compound of the formula IV or V

(IV)

or

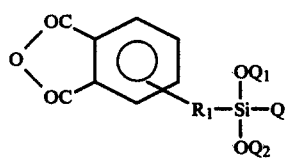
(V)

or a mixture of such compounds, m, n, A, R, R$_1$, Q, Q$_1$, Q$_2$, Z, Z$_2$ and Z$_3$ in the above formulae II to V being as defined under formula I, whilst at least one of Z$_2$, Z$_4$ and Z$_5$ is a

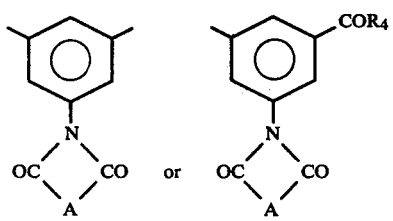

group, a$_1$ is an integer from 1 to 49, the radicals R$_4$ independently of one another are —OH, chlorine, alkoxy with 1–4 C atoms, phenoxy or —NH—Z—NH$_2$ and R$_5$ is —OH, chlorine, alkoxy with 1–4 C atoms, phenoxy or —NH—Z—NH$_2$ or, if Z$_3$ is a cyclic radical and m is 2, R$_5$ together with R$_6$ are a —O— group, the groups —COR$_5$, —COR$_6$ and —COOH are bonded to different C atoms and if Z$_3$ is a cyclic radical and m and/or n are 2, the —COR$_5$ or —COOH group is in the orthoposition to the —COR$_6$ group or to the adjoining carboxamide group, after which the reaction product may or may not be cyclised to the corresponding imide.

Alkoxy groups R$_4$ and R$_5$ and alkyl groups X, Q$_1$, Q$_2$ or Q$_3$ may be straight-chain or branched. Examples of alkoxy and alkyl groups according to the definition are the methoxy, ethoxy, n-propoxy, isopropoxy and n-butoxy group, and the methyl, ethyl, n-propyl, isopropyl, n-butyl, tert.-butyl, n-pentyl, n-hexyl and n-heptyl group.

Preferred alkoxy groups R$_4$ and R$_5$ are methoxy and ethoxy.

Preferred alkyl groups X have 2–4 C atoms, the ethyl and isopropyl group being particularly preferred.

Preferred alkyl groups Q$_1$, Q$_2$ and Q$_3$ are straight-chain groups with 1–6 C atoms.

Y$_1$ and Y$_2$ may have different meanings, but advantageously are groups according to the same definition.

R is preferably a

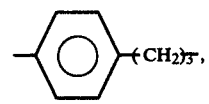

radical, but especially a —(CH$_2$)$_3$— or

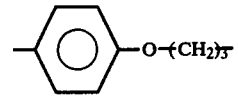

radical.

The radical

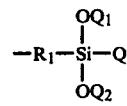

is advantageously bonded to the benzene ring in the ortho-position to the —COOH group or to the —CO—NH—Z—NH—CO— group. Preferably, R$_1$ is —O—(CH$_2$)$_3$— and especially

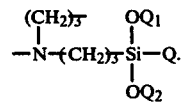

Particularly preferentially, Y$_1$ and Y$_2$ are each a

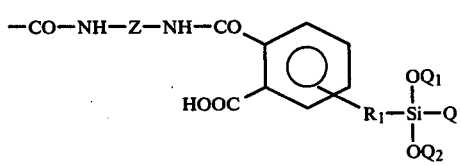

group and especially each a

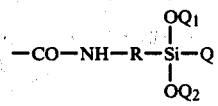

group, in which

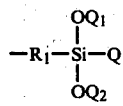

is bonded in the ortho-position to the —COOH or —CO—NH—Z—NH—CO— group, R is $+CH_2+_3$ or

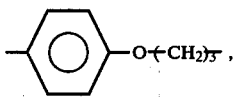

$R_1$ is —O$+CH_2+_3$ or

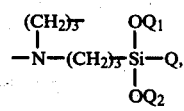

Q is methyl or alkoxy with 1-4 C atoms and $Q_1$ and $Q_2$ are each alkyl with 4 carbon atoms.

Very particularly preferred compounds are polymers of the formula I and the corresponding cyclised imide derivatives, in which $Y_1$ and $Y_2$, and R and $R_1$, have the above preferred meaning, Q is methyl, ethoxy or n-propoxy and $Q_1$ and $Q_2$ are each ethyl or n-propyl.

A is advantageously

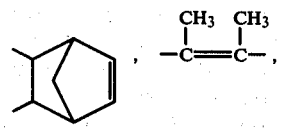

and especially —CH═CH—.

The radicals $R_4$ are preferably each chlorine. If m is 1, $R_5$ is also preferably chlorine. If m is 2, $R_5$ together with $R_6$ are the —O— group, in accordance with the definition given.

Preferred products for use as adhesion promoters are polymers of the formula I, and the corresponding cyclised derivatives, in which a is an integer from 1 to 15, especially approximately from 1 to 10. For the production of crosslinked mouldings, it is preferred to use polymers of the formula I, or corresponding cyclised derivatives, in which a is greater than 15, and in particular equal to or greater than 20.

The proportion, in the polymers mentioned, of groups $Z_1$ and/or $Z_2$ which are

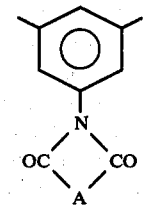

may be up to 100 mol % but it advantageously about 5-50 mol % and especially about 10-30 mol %, based on the total number of mols of acid components employed.

In formula I, the individual symbols Z, $Z_1$, $Z_2$, $Z_3$, m and n may have different meanings.

Radicals Z may be unsubstituted or substituted, for example by halogen atoms, for instance fluorine, chlorine or bromine, or by alkyl or alkoxy groups each with 1-4 C atoms.

Suitable aliphatic radicals Z are in particular straight-chain or branched alkylene groups with 2-12 carbon atoms, especially unsubstituted alkylene groups with 2-10 carbon atoms. The alkylene chain may also be interrupted by hetero-atoms, for example O, S or N atoms.

If Z is a cycloaliphatic radical it may be, for example, the 1,3- or 1,4-cyclohexylene, 1,4-bis-(methylene)-cyclohexane or dicyclohexylmethane group, whilst suitable araliphatic radicals Z are especially 1,3-, 1,4- or 2,4-bis-alkylenebenzene, 4,4'-bis-alkylenediphenyl and 4,4'-bis-alkylene-diphenyl-ether radicals.

If Z is a carbocyclic-aromatic radical, it is preferably a monocyclic, fused polycyclic or non-fused bicyclic aromatic radical, and in the latter case the aromatic nuclei may be bonded to one another by a bridge member.

Examples of suitable bridge members are:

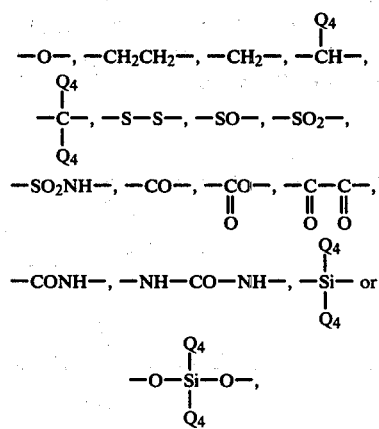

in which $Q_4$ is an alkyl group with 1-6, preferably 1-4, carbon atoms or a phenyl group.

Non-fused bicyclic aromatic radicals Z may also be bonded to one another by two bridge members, such as two —$SO_2$— groups.

If Z is a heterocyclic-aromatic radical, it is in particular a heterocyclic-aromatic 5-membered or 6-membered ring containing O, N and/or S.

If $Z_3$ is an aliphatic radical, it is preferably an unsubstituted, straight-chain or branched alkylene group with 1–12 carbon atoms, especially an unsubstituted alkylene group with 2–10 carbon atoms.

Cycloaliphatic radicals $Z_3$ are especially 5-membered or 6-membered cycloalkylene groups.

If $Z_3$ is a carbocyclic-aromatic radical, the latter preferably contains at least one 6-membered ring; in particular, such radicals are monocyclic radicals, fused polycyclic radicals, or polycyclic radicals with several cyclic, fused or non-fused, systems, which may be bonded to one another directly or by bridge members. Suitable bridge members are those mentioned above in discussing Z.

If $Z_3$ is a heterocyclic-aromatic radical, it is in particular a 5-membered or 6-membered heterocyclic-aromatic ring system which contains O, N and/or S, and may or may not be benzo-fused.

Carbocyclic-aromatic or heterocyclic-aromatic radicals $Z_3$ may also be substituted, for example by nitro groups, alkyl groups with 1–4 carbon atoms, halogen atoms, especially chlorine, silyl groups, sulphonic acid groups or sulphamoyl groups.

Preferably, the individual radicals Z are, independently of one another, an unsubstituted alkylene group with 2–10 carbon atoms or a monocyclic, or non-fused bicyclic, aromatic radical which is unsubstituted or substituted by halogen, or by alkyl or alkoxy groups, each with 1–4 carbon atoms (the aromatic nuclei, in a non-fused bicyclic aromatic radical, being bonded to one another directly or via a —O—, —$CH_2$— or —$SO_2$— bridge member), or an unsubstituted monocyclic araliphatic radical.

The individual radicals $Z_3$ are preferably, independently of one another, an unsubstituted alkylene group with 2–10 C atoms or an unsubstituted monocyclic, fused polycyclic or non-fused bicyclic aromatic radical, (the aromatic nuclei, in a non-fused bicyclic aromatic radical, being bonded to one another via a —O—, —$SO_2$— or —CO— bridge member).

Preferred compounds of the formula I, and the corresponding cyclised derivatives, are those in which a is an integer from 1 to 50, especially from 1 to 15, the radicals $Y_1$ and $Y_2$ are each a

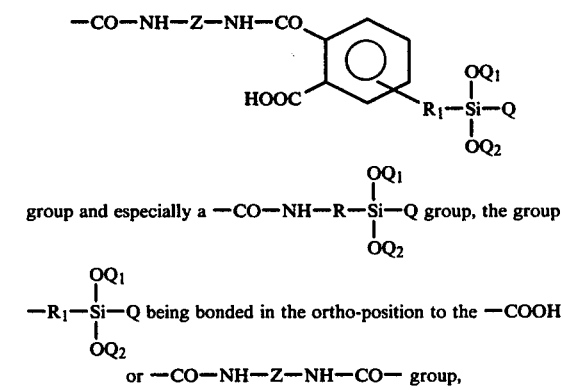

group and especially a —CO—NH—R—Si(OQ$_1$)(OQ$_2$)—Q group, the group —R$_1$—Si(OQ$_1$)(OQ$_2$)—Q being bonded in the ortho-position to the —COOH or —CO—NH—Z—NH—CO— group,

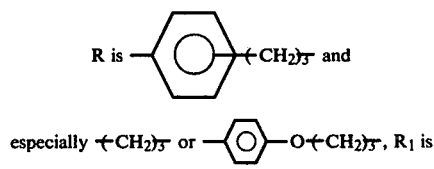

-continued

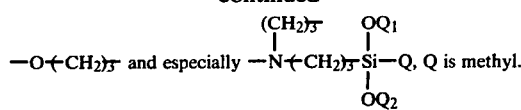

or alkoxy with 1–4 C atoms and $Q_1$ and $Q_2$ are each alkyl with 1–4 C atoms, especially those in which a, $Y_1$, $Y_2$, R, $R_1$, Q, $Q_1$ and $Q_2$ have the abovementioned preferred meaning and the radicals Z are each a 1,3- or 1,4-phenylene group, or a 4,4'-diphenylmethane, 4,4'-diphenyl-ether or 4,4'-diphenylsulphone radical, the radicals $Z_3$ are each a 1,3-phenylene or 1,4-phenylene group or unsubstituted alkylene with 4–10 C atoms, if m and n are 1, or are each a benzenetriyl group if m is 1 and n is 2, or are each a benzenetetrayl group or the benzophenone ring system if m and n are 2, and at least one of the radicals $Z_1$ and $Z_2$, and preferably about 5–50 mol % of these, is a

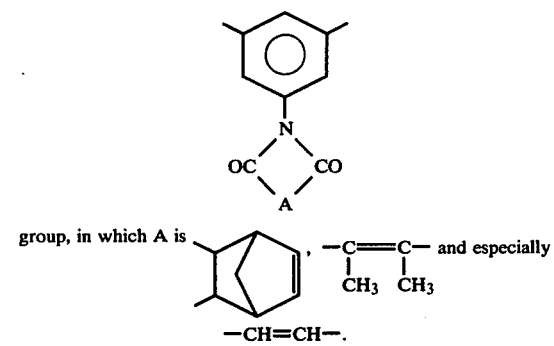

—CH=CH—.

Particularly preferred compounds of the formula I, and the corresponding cyclised imide derivatives, are those in which $Y_1$, $Y_2$, R, $R_1$, Q, $Q_1$ and $Q_2$ have the above-mentioned preferred meanings, a is an integer from 1 to 50, preferably from 1 to 10, and m and n are each 1, Z is a 1,3- or 1,4-phenylene group, or a 4,4'-diphenylmethane or 4,4'-diphenyl-ether radical and $Z_3$ is a 1,3-phenylene or 1,4-phenylene group, but only one of Z and $Z_3$ is a 1,4-phenylene group; or m is 1 and n is 2, Z is a 1,3- or 1,4-phenylene group, or a 4,4'-diphenylmethane or 4,4'-diphenyl-ether radical and $Z_3$ is a benzenetriyl group;

m and n are each 2, Z is a 1,3- or 1,4-phenylene group, or a 4,4'-diphenylmethane or 4,4'-diphenyl-ether radical and $Z_3$ is a benzenetetrayl group or the benzophenone ring system.

and in which at least one of $Z_1$ and $Z_2$, and preferably about 10–30 mol % of $Z_1$ and $Z_2$, is a

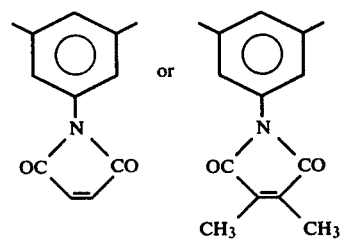

group.

Very particularly preferred compounds, amongst the above, are those in which Q is methyl, ethoxy or n-propoxy and $Q_1$ and $Q_2$ are each ethyl or n-propyl.

The reaction of a compound of the formula II or III with a compound of the formula IV and/or V is carried out in a manner known per se, preferably in an anhydrous inert organic solvent at temperatures between about $-20°$ C. and $+150°$ C., especially about $-15°$ C. to $+50°$ C.

Examples of organic solvents which may be employed are chlorinated or non-chlorinated aromatic hydrocarbons, for example benzene, toluene, xylenes and chlorobenzene; chlorinated or non-chlorinated aliphatic hydrocarbons, for example n-pentane, n-hexane, methylene chloride, chloroform, tetrachloroethane and tetrachloroethylene; aliphatic and cycloaliphatic ketones, for example acetone, methyl ethyl ketone, cyclopentanone and cyclohexanone; cyclic ethers, for example tetrahydrofuran, tetrahydropyran and dioxane; cyclic amides, for example N-methyl-2-pyrrolidone, N-acetyl-2-pyrrolidone and N-methyl-ε-caprolactam; N,N-dialkylamides of aliphatic monocarboxylic acids with 1-3 carbon atoms in the acid part, for example N,N-dimethylformamide, N,N-dimethylacetamide, N,N-diethylacetamide and N,N-dimethylmethoxyacetamide; hexamethylphosphorotriamide (hexametapol); N,N,N',N'-tetramethylurea; tetrahydrothiophene dioxide (sulpholan); dialkylsulphoxides, for example dimethylsulphoxide and diethylsulphoxide; phenol and cresols.

The reaction can also be carried out in mixtures of such solvents.

Preferred solvents are N,N-dialkylamides of aliphatic monocarboxylic acids with 1-3 carbon atoms in the acid part, especially N,N-dimethylformamide and N,N-dimethylacetamide, and cyclic amides, for example N-methyl-2-pyrrolidone.

The compounds of the formula III are reacted with the compounds of the formula IV and/or V in a molar ratio of at least 2:1. If $a_1$ in formula III is 1, the compound of the formula III is advantageously used in the stoichiometric amount or in a slightly smaller amount than this. For the reaction with oligomers or polymers of the formula III ($a_1$ greater than or equal to 1), the reactants are preferably employed in the stoichiometric amount.

If the compounds of the formula IV or V are reacted with oligomers or polymers of the formula III, the latter are advantageously used in the form of their solutions, as obtained from their preparation.

To prepare compounds of the formula I, in which $Y_1$ and $Y_2$ are each a

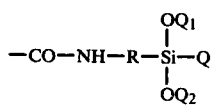

group, a compound of the formula II or III, in which $R_4$ and/or $R_5$ are not a $-NH-Z-NH_2$ and $R_4$ is preferably alkoxy with 1-4 C atoms or phenoxy and especially chlorine, and if m and n are 1 or m is 1 and n is 2, $R_5$ is alkoxy with 1-4 C atoms or phenoxy and especially chlorine, and if m and n are 2, $R_5$ together with $R_6$ is the $-O-$ group, is reacted with a compound of the formula IV or with a mixture of two different compounds of the formula IV.

To prepare compounds of the formula I, in which $Y_1$ and $Y_2$ are each a

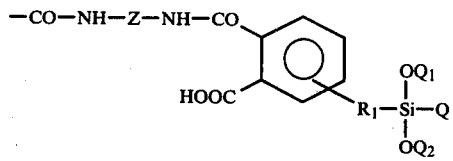

group, a compound of the formula V or a mixture of two different compounds of the formula V is reacted with a compound of the formula II or III, in which $R_4$ or $R_5$ is $-NH-Z-NH_2$.

Analogously, compounds of the formula I, in which one of $Y_1$ and $Y_2$ is a

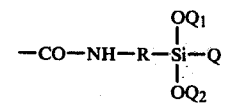

group and the other is a

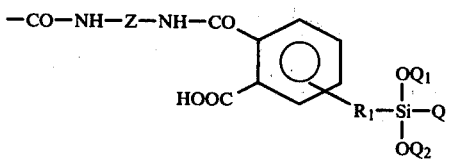

group, and prepared by reacting a compound of the II or III, in which one of the terminal functional groups $R_4$ and $R_5$ is not $-NH-Z-NH_2$ and the other is $-OH$, alkoxy with 1-4 C atoms, phenoxy or chlorine, or, if m is 2, $R_5$ together with $R_6$ is $-O-$, with a mixture of a compound of the formula IV and a compound of the formula V.

In all these cases, the compound of the formula IV and/or V is preferably employed in the stoichiometric amount.

After completion of the reaction, the solvents can, if desired, be removed in the usual manner, for example by distilling off, if appropriate under reduced pressure.

The starting compounds of the formula II are in the majority of cases described in German Offenlegungsschriften Nos. 2,626,768 and 2,626,795 and may all be prepared in accordance with the method disclosed there.

Compounds of the formula III can be prepared in a manner known per se, by reacting a compound of the formula VI

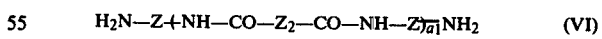

with an excess of a compound of the formula II and/or of a compound of the formula VII

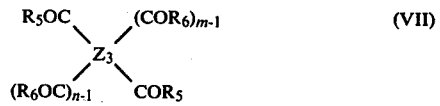

$a_1$, m, n, Z, $Z_2$, $Z_3$, $R_5$ and $R_6$ being as defined above.

The compounds of the formula VI can, for their part, be obtained by reacting an excess of diamine $H_2N-Z-NH_2$ with a dicarboxylic, tricarboxylic or tetracarboxylic acid derivative of the formulae VIII and/or IX

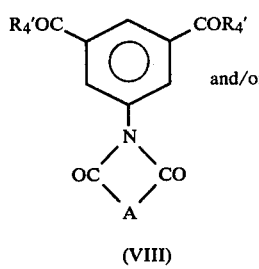
(VIII)

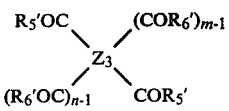
(IX)

in which m, n, A and $Z_3$ are as defined above, the radicals $R_4'$ independently of one another are —OH, chlorine, alkoxy with 1–4 C atoms or phenoxy and the radicals $R_5'$ independently of one another are —OH, chlorine, alkoxy with 1–4 C atoms or phenoxy, or, if m and/or n is 1, $R_5'$ together with $R_6'$ is —O—, the groups —$COR_5'$ and —$COR_6'$ are bonded to different C atoms and, if $Z_3$ L is a cyclic radical and m and/or n is 2, the —$COR_5'$ group or groups are each in the ortho-position to a —$COR_6'$ group.

Compounds of the formula III, in which $R_4$ and $R_5$ are not —NH—Z—$NH_2$, can also be prepared by reacting a diamine $H_2N$—Z—$NH_2$ with an excess of a mixture of different compounds of the formulae VIII and IX.

The condensation of a compound of the formula VI with a compound of the formula II and/or a compound of the formula VII, and the preparation of compounds of the formula III or VI from diamines $H_2N$—Z—$NH_2$ and dicarboxylic, tricarboxylic or tetracarboxylic acid derivatives of the formulae VIII and/or IX is carried out in a manner known per se, advantageously at temperatures from about −50° C. to +300° C. The condensation can be carried out in the melt or, preferably, in an inert organic solvent or a solvent mixture. For condensation in solution, temperatures of about −20° C. to +200° C., very particularly about −20° C. to +50° C., are preferred. In the said reactions, it may under certain circumstances be advantageous to add known polymerisation inhibitors, for example hydroquinones, pyrocatechol or cresols, for example di-tert.-butylcresol.

Examples of suitable inert organic solvents are those mentioned above in connection with the reaction of compounds of the formula II or III with the compounds of the formula IV and/or V.

The hydrochloric acid formed during the condensation or polycondensation of compounds of the formulae II, VII, VIII or IX, in which $R_4$, $R_4'$, $R_5$ or $R_5'$ is chlorine, with the diamines $H_2N$—Z—$NH_2$ or the diamines of the formula III can be removed by neutralisation with basic compounds, for example calcium hydroxide or triethylamine, or by reaction with an epoxide compound, for example ethylene oxide or propylene oxide, and by washing out with a suitable solvent, for example water. The condensation reactions are advantageously carried out with exclusion of moisture, for example in an inert gas atmosphere, for instance nitrogen.

The aminosilanes of the formula IV are known or can be prepared in a manner known per se. The compounds of the formula V can be prepared by reacting a compound of the formula X

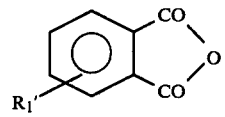
(X)

in which $R_1'$ is —O—$CH_2CH=CH_2$ or

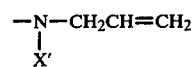

and X' is alkyl with 2–7 C atoms, cycloalkyl with 5–7 C atoms, benzyl or allyl, with a silane of the formula XI

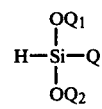
(XI)

in which Q, $Q_1$ and $Q_2$ are as defined under formula I. The reaction is advantageously carried out in an anhydrous organic medium and in the presence of a catalyst. Examples of catalysts which can be used are organic peroxides, for instance tert.-butyl hydroperoxide, di-tert.-butyl peroxide, benzoyl peroxide, diacyl peroxides and cumene hydroperoxide, or platinum and palladium catalysts, for example platinum/charcoal catalysts or $PtCl_6H_2$ catalysts.

Examples of suitable inert organic solvents are aromatic hydrocarbons, for instance benzene, toluene and xylenes, cyclic ethers, for instance tetrahydrofuran, tetrahydropyran and dioxane, or ethylene glycol mono-alkyl ethers and dialkyl ethers, with 1–4 C atoms in each alkyl part, for instance ethylene glycol monomethyl ether, monoethyl ether, diethyl ether and di-n-butyl ether. Aromatic hydrocarbons are preferred.

The reaction is advantageously carried out under a protective gas, for example nitrogen or argon.

The reaction temperatures are in general approximately between 80° and 150° C.; reaction temperatures between approximately 90° and 120° C. are preferred.

The compounds of the formula XI are known.

Compounds of the formula X, in which $R_1'$ is a diallylamino group, can be prepared, for example, by reacting aminophthalic acid or the corresponding alkali metal salts or alkaline earth metal salts with allyl halides and cyclising the resulting N,N-diallylaminophthalic acid. Compounds of the formula X, in which $R_1'$ is an allyloxy group, can be obtained by reacting hydroxyphthalic anhydride with an allyl halide. Finally, compounds of the formula X, in which $R_1'$ is a

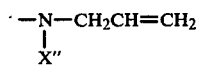

group and X" is alkyl with 2–7 C atoms, cycloalkyl with 5–7 C atoms or benzyl, can be prepared by reacting a compound of the formula XII

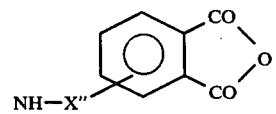
(XII)

in which X" has the abovementioned meaning, with an allyl halide.

These reactions with allyl halides, especially allyl bromide or allyl chloride, are advantageously carried out in a polar medium, especially in an aqueous medium, at temperatures between about 0° and 100° C. and preferably in the presence of a base, for instance an alkali metal carbonate or hydroxide, for example potassium carbonate, potassium hydroxide or sodium hydroxide.

The cyclisation of polymers according to the invention, of the polyamidoacid category or polyamide-amidoacid category, to the corresponding polyimides or polyamide-imides, can be carried out in a manner known per se, chemically or thermally.

Chemical cyclisation is advantageously effected by treatment with a dehydrating agent, used by itself or mixed with a tertiary amine. Examples of suitable dehydrating agents are acetic anhydride, propionic anhydride and dicyclohexylcarbodiimide, used by themselves, or as a mixture with, for example, triethylamine.

Thermal cyclisation is effected by heating to temperatures of about 50°–250° C., preferably about 100°–150° C., in the presence or absence of an inert organic solvent and/or an azeotropic entraining agent, for example xylenes or toluene. At temperatures above 150° C., at least partial crosslinking also generally occurs.

Compounds of the formula I, and the corresponding cyclised imide derivatives, in which a is an integer having a value of about 1–15, especially about 1–10, are valuable adhesion promoters, especially between inorganic solids and organic resins, and may be used for a large number of applications in the adhesives industry and in the lacquer-using and plastics-processing industries.

The following are examples of some fields of use: improving the adhesion of special sealants, for example polysulphides, polyurethanes and polyacrylates, to various substrates, for example glass, aluminium and ceramics; encapsulating mineral fillers so as to improve the mechanical properties of the products prepared therewith, for example in the case of sand-filled masks and cores used in the foundry industry, mineral-filled cable mixtures or other mineral-filled plastics, for example filled thermosetting resins, for instance quartz-filled epoxide resins and filled unsaturated polyesters, filled thermoplastics, for instance polyamide-6,6 and polyethylene terephthalate, and filled elastomers, for instance natural rubber and synthetic rubber; and incorporation in adhesives, adhesive compositions and lacquers, for example adhesive compositions containing epoxide resins, and lacquers based on epoxides, polyacrylates, polyurethanes and vinyl chloride copolymers. However, the compounds mentioned are especially suitable for the manufacture of reinforced plastics, especially glass fibre-reinforced plastics, in particular composite materials, for instance laminates, in order to improve the adhesion between the substrate or matrix and the plastic applied thereto. The substrate per se may be in any desired form, for example in the form of fibres, fabrics or nonwovens, and preferably consists of glass or of mineral materials, for example quartz, mineral wool, asbestos, mica or metal fibres and foils. Examples of suitable plastics for the manufacture of such laminates are acrylates and polyester, epoxide, silicon, melamine, phenolic and furan resins, and also polyamides, polyamidoacids and polyimides, but especially polymers crosslinkable via C=C double bonds, for instance unsaturated polyesters, homopolymers and copolymers containing maleimidyl and nadicimidyl groups, their precursors and their mixtures with other polymers.

Relative to comparable composite materials which have been manufactured using known silicon-containing adhesion promoters, especially those of the type mentioned at the outset, glass fibre-reinforced composite materials manufactured using the adhesion promoters according to the invention are distinguished especially by improved resistance to thermal oxidation, improved dielectric properties after exposure to moisture, and/or lower water absorption. The adhesion promoters of the invention are also distinguished by good wetting of the substrates.

The adhesion promoters according to the invention are advantageously applied in the form of solutions in suitable organic solvents, for example N,N-dimethylformamide, N,N-dimethylacetamide, N-methyl-2-pyrrolidone, acetone, methyl ethyl ketone, tetrahydrofuran or dioxane, using conventional techniques.

Polymers of the formula I, and the corresponding cyclised imide derivatives, in which a is greater than 15, and in particular is at least about 20, may be used for the production of shaped articles having a particularly high degree of crosslinking, for example fibres, films (sheets), coating compositions, foams, laminates, compression mouldings and the like, in a manner known per se, by heating to temperatures between about 50° and 350° C., if desired in the presence of conventional additives, for example pigments, fillers and the like. The resulting crosslinked polymers containing imidyl groups and siloxane groups are insoluble in organic solvents. They are distinguished by good mechanical, electrical and thermal properties, in particular good corona resistance and high resistance to thermal oxidation. Non-cyclised polymers of the formula I with a greater than about 15 and especially with a at least equal to 20, are distinguished by good processability from corresponding solutions. Crosslinking via the imidyl groups can also be effected by exposure to light, especially UV light, and this permits selective stepwise crosslinking, in that preliminary crosslinking, via the imidyl groups, is first effected under the action of light, after which crosslinking via the silyl groups is effected thermally. Such stepwise crosslinking can under appropriate circumstances also be carried out thermally.

PREPARATION EXAMPLES

Example 1

In a sulphonation flask, 3.24 g (0.03 mol) of m-phenylenediamine are dissolved in 160 ml of anhydrous N,N-dimethylacetamide (DMA) under a nitrogen atmosphere, and the solution is cooled to between −15° C. and −20° C. 6.52 g (0.02 mol) of 5-dimethylmaleimidyl isophthalic acid dichloride are added in portions, with stirring, under conditions such that the temperature does not exceed −15° C. The reaction mixture is stirred for a further 30 minutes at −15° C. and then for one hour at 20°–25° C. and thereafter is again cooled to −15° C., whereupon a solution of 4.04 g (0.04 mol) of triethylamine in 20 ml of DMA is added dropwise. A fine white precipitate forms. After stirring for one hour at 20°–25° C., the mixture is cooled to 0° C. 6.44 g (0.02 mol) of 3,3′,4,4′-benzophenonetetracarboxylic acid dianhydride are then added in portions. After stirring for 1 hour at 20°–25° C., the mixture is again cooled to 0° C., after which a solution of 4.39 g (0.02 mol) of γ-aminopropyl-di-n-propoxymethylsilane in 20 ml of DMA is added dropwise. Stirring is then continued for 1 hour at 20°-25° C., after which the reaction mixture is filtered to remove the triethylamine hydrochloride which has precipitated. The 10% polyamidoacid solution obtained can be used for finishing glass fibres, from which laminates can be produced.

Example 2

In a sulphonation flask, 4.87 g (0.045 mol) of m-phenylenediamine are dissolved in 160 ml of anhydrous DMA under a nitrogen atmosphere and the solution is cooled to between −15° and −20° C. A mixture of 6.09 g (0.03 mol) of isophthalic acid dichloride and 5.96 g (0.02 mol) of 5-maleimidyl-isophthalic acid dichloride is added in portions, with stirring, under conditions such that the reaction temperature does not exceed −15° C. After stirring for one hour at this temperature, a solution of 2.19 g (0.01 mol) of γ-aminopropyl-di-n-propoxy-methylsilane in 10 ml of DMA is added dropwise and the reaction mixture is stirred for a further hour at −15° C. A solution of 10.12 g (0.1 mol) of triethylamine in 30 ml of DMA is then added dropwise, at this temperature, and stirring is continued for 1 hour. After warming to 20°-25° C., the triethylamine hydrochloride which has precipitated is filtered off and the resulting polyamide solution is used for finishing glass fibres.

Example 3

Using the procedure described in Example 2, 7.07 g (0.0336 mol) of trimellitic acid anhydride chloride, 5.21 g (0.0144 mol) of 5-nadicimidyl-isophthalic acid dichloride, 8.01 g (0.04 mol) of 4,4'-diaminodiphenyl-ether, 3.51 g (0.016 mol) of γ-aminopropyl-di-n-propoxy-methylsilane and 6.31 g (0.0624 mol) of triethylamine are reacted in 230 ml of anhydrous DMA. The polyamidoacid solution obtained can be used for finishing glass fibres.

Example 4

Using the procedure described in Example 2, 3.24 g (0.03 mol) of m-phenylenediamine, 6.69 g (0.028 mol) of sebacic acid dichloride, 2.08 g (0.007 mol) of 5-maleimidyl-isophthalic acid dichloride, 2.19 g (0.01 mol) of γ-aminopropyl-di-n-propoxymethylsilane and 7.08 g (0.07 mol) of triethylamine are reacted in 140 ml of anhydrous DMA. The resulting polyamide solution can be used for finishing glass fibres.

The preparation of 5-dimethylmaleimidyl-isophthalic acid dichloride, 5-maleimidyl-isophthalic acid dichloride and 5-nadicimidyl-isophthalic acid dichloride, used in the above examples, is described in German Offenlegungsschriften Nos. 2,626,768 and 2,626,795.

Example 5

In a sulphonation flask, 6.20 g (0.031 mol) of 4,4'-diaminodiphenyl-ether (DDA) are dissolved in 50 ml of anhydrous N,N'-dimethylacetamide under a nitrogen atmosphere, and the solution is cooled to between −15° and −20° C. 1.78 g (0.006 mol) of 5-maleimidyl-isophthalic acid dichloride (MIP) are added in portions, with stirring, under conditions such that the temperature does not exceed −15° C. The reaction mixture is stirred for a further 30 minutes at −15° C. and then for one hour at 20° to 25° C., after which it is again cooled to −15° C. and 1.21 g (0.012 mol) of triethylamine are added dropwise. A fine, white precipitate forms. After stirring for one hour at 20° to 25° C., the mixture is cooled to 0° C. 5.23 g (0.024 mol) of pyromellitic acid dianhydride (PMDA) are then added in portions. After stirring for one hour at 20° to 25° C., the mixture is again cooled to 0° C., after which 1.31 g (0.002 mol) of 4-N,N'-bis-[3-(tri-n-propoxy)-silyl-propyl]-aminophthalic anhydride are added dropwise. The reaction mixture is then stirred for a further hour at 20° C., after which it is filtered to remove the triethylamine hydrochloride which has precipitated. The 10% polyamidoacid solution obtained is cast on a glass plate to produce a film and is dried in a vacuum oven for 24 hours at 60° to 150° C., for 2 hours at 150° to 250° C. and for 3 hours at 250° C. A transparent, flexible and tough film is obtained.

Example 6

In a sulphonation flask, 14.56 g (0.04 mol) of 5-nadicimidyl-isophthalic acid dichloride are dissolved in 150 ml of anhydrous N,N'-dimethylacetamide under a nitrogen atmosphere, and the solution is cooled to between −15° and −20° C. A solution of 17.68 g (0.08 mol) of γ-aminopropyl-triethoxysilane in 25 ml of N,N'-dimethylacetamide is added dropwise at −15° C., with stirring. After stirring for one hour at this temperature, a solution of 8.09 g (0.08 mol) of triethylamine in 28 ml of N,N'-dimethylacetamide is added dropwise and the reaction mixture is stirred for a further hour. After warming to 20°-25° C., the triethylamine hydrochloride which has precipitated is filtered off. The solution of the diamide obtained can be used for finishing glass fibres.

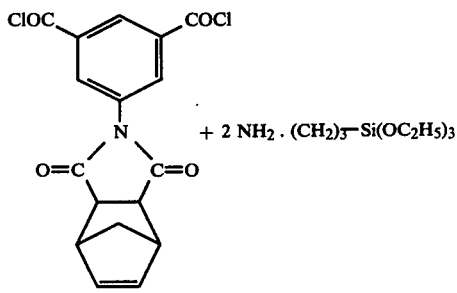

Example 7

In a sulphonation flask, 3.24 g (0.03 mol) of 1,3-phenylenediamine are dissolved in 80 ml of anhydrous N,N'-dimethylacetamide under a nitrogen atmosphere and the solution is cooled to between −15° and −20° C. 3.26 g (0.01 mol) of 5-(dimethylmaleimidyl)-isophthalic acid dichloride are added in portions, with stirring, under conditions such that the temperature does not exceed −15° C. The reaction mixture is stirred for a further hour at −15° C. Thereafter, 3.58 g (0.015 mol) of sebacic acid dichloride are added dropwise at this temperature, and stirring is continued for 30 minutes. 5.06 g (0.05 mol) of triethylamine are then added dropwise and after stirring for one hour at 20° to 25° C. the mixture is cooled to 0° C. A solution of 3.66 g (0.01 mol) of 3-(γ-methyl-di-n-propoxy-silyl)-propoxy-phthalic anhydride in 34 ml of N,N'-dimethylacetamide is then added dropwise, the mixture is stirred for a further hour at 20° to 25° C. and the triethylamine hydrochloride which has precipitated during the reaction is filtered off. The resulting polyamidoacid solution can be used for finishing glass fibres, from which laminates are produced.

Use Examples

(a) Impregnation of glass fibre fabrics

A glass fibre fabric made from so-called E-glass, with satin weave and weighing 280 g/m², is first thermally desized to about 0.1% by weight residual size content and is then impregnated with 2% solutions of the adhesion promoters or of the commercially available adhesion promoters listed below. The adhesion promoter solutions are applied by immersion, with an impregnation speed of 0.5 m/minute, and the impregnated material is then dried for 20 minutes at 180° C. in a circulating air oven.

The prepregs obtained contain from 0.09 to 0.11% by weight, based on glass, of adhesion promoter.

The following are used as adhesion promoters (finishes):

(1) No adhesion promoter
(2) Vinyl-tri-(2-methoxyethoxy)-silane ("Silan A 172" from Messrs. Union Carbide); 2% solution in N,N-dimethylformamide (DMF)
(3) γ-Aminopropyl-triethoxysilane ("Silan A 1100" from Messrs. Union Carbide); 2% solution in DMF
(4) Adhesion promoter solution according to Preparation Example 1, diluted to 2% by weight with DMF
(5) Adhesion promoter solution according to Preparation Example 2, diluted to 2% by weight with DMF
(6) Adhesion promoter solution according to Preparation Example 3, diluted to 2% by weight with DMF
(7) Adhesion promoter solution according to Preparation Example 4, diluted to 2% by weight with DMF
(8) Adhesion promoter solution according to Preparation Example 6, diluted to 2% by weight with DMF
(9) Adhesion promoter solution according to Preparation Example 7, diluted to 2% by weight with DMF

(b) Production of copper-covered laminate sheets 1.0 mol of N,N'-4,4'-diphenylmethane-bis-maleimide is dissolved in 500 g of furfuryl alcohol at 100° C. and the solution is cooled to 25° C. 0.4 mol of 4,4'-diaminodiphenylmethane is dissolved in 200 g of methylglycol at 25° C. The two solutions are combined and mixed thoroughly. The glass fibre fabrics finished in accordance with section (a) are impregnated with this mixed solution by the immersion process at 25° C. and are then dried in a circulating air oven for 18 minutes at 180° C.; the resulting prepregs contain 39% by weight of resin. 10 layers of the impregnated fabric are then pressed hot between two 35 microns thick copper foils which have been pretreated by electrolytic surface coating with brass. The press is first kept under light contact pressure for 2 to 3 minutes; the pressure is then raised to 40 kp/cm² and the assembly is pressed for 1 hour at 180° C. The test specimens are then taken out of the press and post-cured for a further 6 hours in an oven at 240° C.; the resulting laminate sheets contain 35% by weight of resin.

Properties of the resulting copper-covered laminate sheets Flexural strength in N/mm² according to ISO/R 178

(a) Initial value
(b) After 10 days' aging at 270° C.

Water absorption

In % by weight at 23° C. after 24 hours. The measurements are carried out on flexural test specimens according to VSM Standard Specification 77,103.

Dielectric loss factor tg δ/50 c/s according to DIN 53,483

(a) Initial value measured at 23° C.
(b) After 6 hours' storage in boiling water Dielectric constant $\epsilon_r$/50 c/s according to DIN 53,483

(a) Initial value measured at 23° C.
(b) After 6 hours' storage in boiling water
ISO/R = International Standards Organisation/-Recommendations
VSM = Verein Schweizerischer Maschinenindustrieller
DIN = Deutsche Industrie Norm The results are summarised in Table I which follows. The numbering of the experimental products is the same as under (a).

Table I

| | \multicolumn{9}{c}{(Test values of the laminate sheets according to Use Example b)} |
|---|---|---|---|---|---|---|---|---|---|
| | \multicolumn{9}{c}{Adhesion promoter - Product No.} |
| | 1 | 2 | 3 | 4 | 5 | 6 | 7 | 8 | 9 |
| Flexural strength N/mm², initial value | 422.3 | 401 | 586.7 | 469.3 | 484.5 | 523.7 | 456.5 | 451.3 | 313.8 |
| After 10 days' aging at 270° C. | 282.4 | 108.8 | 162.8 | 361.1 | 341.4 | 330.6 | 352.4 | 277.2 | 254.4 |
| Water absorption in % by weight after 24 hours at 23° C. | 0.54 | 0.28 | 0.29 | 0.14 | 0.24 | 0.20 | 0.22 | 0.49 | 0.29 |
| Dielectric loss factor, δ/50 c/s, initial value | 1.08 | 1.15 | 2.71 | 0.24 | 0.24 | 0.28 | 0.28 | 0.27 | 0.28 |
| After 6 hours' storage in boiling water | 6.57 | 2.81 | 4.22 | 0.36 | 0.63 | 1.66 | 0.45 | 0.41 | 0.45 |
| Dielectric constant $\epsilon_r$/50 c/s, initial value | 5.1 | 5.4 | 5.1 | 5.0 | 4.9 | 5.4 | 5.0 | 5.1 | 5.1 |
| After 6 hours' storage in boiling water | 6.9 | 5.8 | 5.5 | 5.2 | 5.3 | 5.8 | 5.2 | 5.3 | 5.1 |

What we claim is:
1. A compound of the formula I

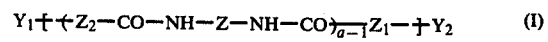

$$Y_1 + (Z_2 - CO - NH - Z - NH - CO)_{\overline{a-1}} Z_1 +Y_2 \qquad (I)$$

in which $Y_1$ and $Y_2$ independently of one another are a

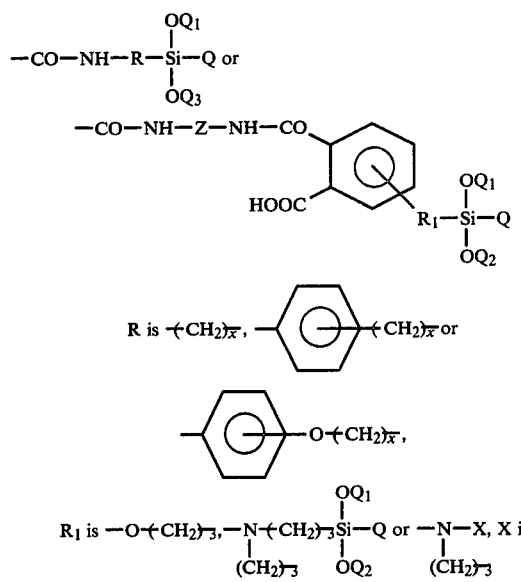

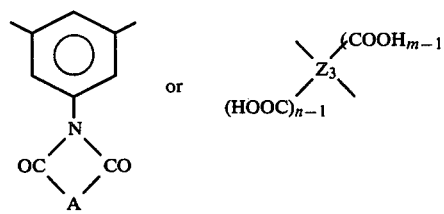

with 2–7 C atoms, cycloalkyl with 5–7 C atoms or benzyl, Q is methyl, phenyl or —OQ₃, Q₁, Q₂ and Q₃ independently of one another are alkyl with 1–6 C atoms or phenyl, x is an integer from 2 to 4, a is an integer from 1 to 50, the individual radicals Z independently of one another are an aliphatic radical with at least 2 C atoms, or a cycloaliphatic, araliphatic, carbocyclic-aromatic or heterocyclic-aromatic radicals and Z₁ and the individual radicals Z₂ independently of one another are a

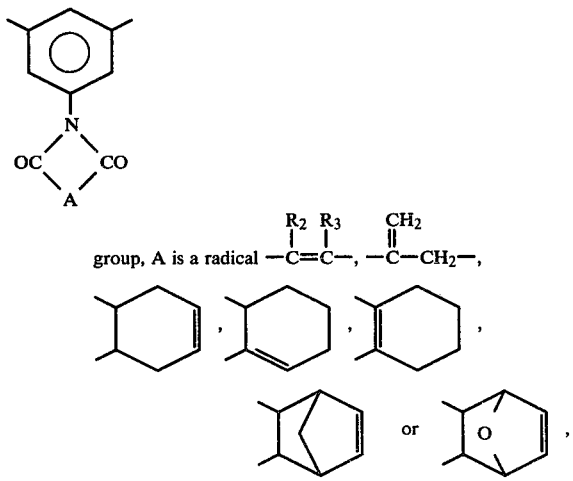

R₂ and R₃ independently of one another are hydrogen or methyl, the individual values m and n independently of one another are 1 or 2 and the individual radicals Z₃ independently of one another are an aliphatic radical with at least 2 C atoms, or a cycloaliphatic, carbocyclic-aromatic or heterocyclic-aromatic radical, in which the carboxamide and carboxyl groups are bonded to different C atoms and carboxyl groups bonded to cyclic radicals Z₃ are each in the ortho-position to a carboxamide group, and the corresponding cyclised imide derivative.

2. A compound of the formula I according to claim 1, and the corresponding cyclised imide derivative, in which a is an integer from 1 to 50, the radicals Y₁ and Y₂ are each a

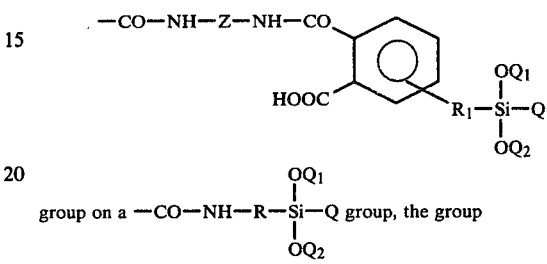

group on a —CO—NH—R—Si(OQ₁)(OQ₂)—Q group, the group

—R₁—Si(OQ₁)(OQ₂)—Q being bonded in the ortho-position to the —COOH or —CO—NH—Z—NH—CO— group, R is —⟨phenyl⟩—(CH₂)ₓ̄, —(CH₂)ₓ̄ or —⟨phenyl⟩—O—(CH₂)₃, R₁ is —O—(CH₂)₃ or —N—(CH₂)₃Si(OQ₁)(OQ₂)—Q, Q is methyl or alkoxy with 1–4 C atoms and Q₁ and Q₂ are each alkyl with 1–4 C atoms.

3. A compound of the formula I according to either of claims 1 or 2, and the corresponding cyclised imide derivative, in which the radicals Z are each a 1,3- or 1,4-phenylene group, or a 4,4'-diphenylmethane, 4,4'-diphenylether or 4,4'-diphenylsulphone radical, the radicals Z₃ are each a 1,3- or 1,4-phenylene group or unsubstituted alkylene with 4–10 C atoms, if m and n are 1, or are each a benzenetriyl group if m is 1 and n is 2, or are each a benzenetriyl group if m is 1 and n is 2, or are each a benzenetetrayl group or the benzophenone ring system if m and n are 2, and at least one of the radicals Z₁ and Z₂, and about 5–50 mol % of these, is a

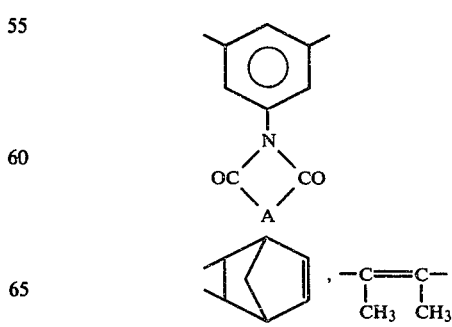

or —CH=CH—.

4. A compound of the formula I according to either of claims 1 or 2, in which a is an integer from 1 to 50, m and n are 1, Z is a 1,3- or a 1,4-phenylene group, or a 4,4'-diphenylmethane or 4,4'-diphenylether radical and $Z_3$ is a 1,3-phenylene or 1,4-phenylene group, but only one of Z and $Z_3$ is a 1,4-phenylene group, and in which about 10-30 mol % of $Z_1$ and $Z_2$ are a

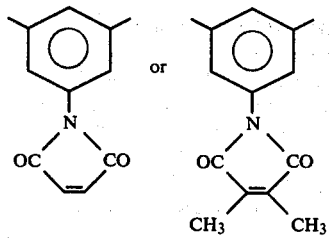

group.

5. A compound of the formula I according to either of claims 1 or 2, and the corresponding cyclised imide derivative, in which a is an integer from 1 to 50, m is 1 and n is 2, Z is a 1,3- or 1,4-phenylene group, or a 4,4'-diphenylmethane or 4,4'-diphenylether radical and $Z_3$ is a benzenetriyl group, and in which about 10-30 mol % of $Z_1$ and $Z_2$ are a

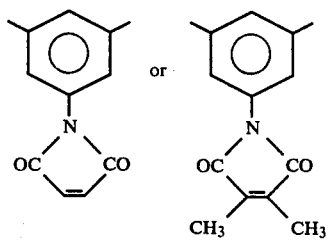

group.

6. A compound of the formula I according to either of claims 1 or 2, and the corresponding cyclised imide derivative, in which a is an integer from 1 to 50, m and n are each 2, Z is a 1,3- or 1,4-phenylene group, or a 4,4'-diphenylmethane or 4,4'-diphenyl-ether radical and $Z_3$ is a benzenetetrayl group or the benzophenone ring system, and in which about 10-30 mol % of $Z_1$ and $Z_2$ are a

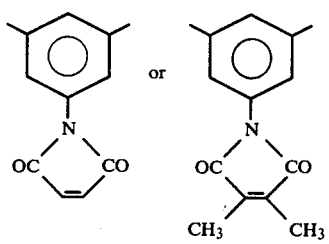

group.

7. A process for the preparation of a compound of the formula I according to claim 1 and of the corresponding cyclised imide derivative, wherein, if a is 1, a compound of the formula II

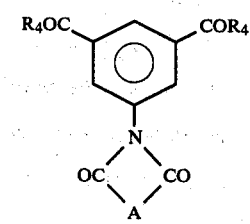

and if a>1, a compound of the formula III

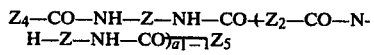

in which $Z_4$ and $Z_5$ independently of one another are a

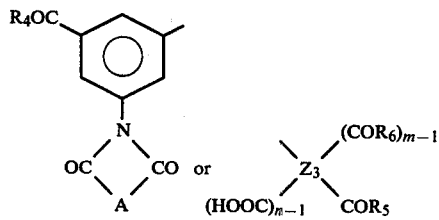

group, is reacted with an essentially stoichiometric amount of a compound of the formula IV or V

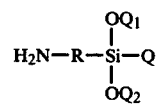

or

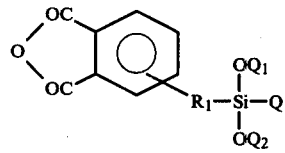

or of a mixture of such compounds, m, n, A, R, $R_1$, Q, $Q_1$, $Q_2$, Z, $Z_2$ and $Z_3$ in the above formulae II to V being as defined in claim 1, whilst at least one of $Z_2$, $Z_4$ and $Z_5$ is a

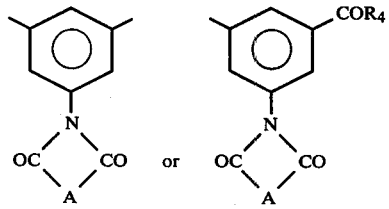

group, $a_1$ is an integer from 1 to 49, the radicals $R_4$ independently of one another are —OH, chlorine, alkoxy with 1-4 C atoms, phenoxy or —NH—Z—$NH_2$ and $R_5$ is —OH, chlorine, alkoxy with 1-4 C atoms, phenoxy or —NH—Z—$NH_2$ or, if $Z_3$ is a cyclic radical and m is 2, $R_5$ together with $R_6$ are a —O— group, the groups —$COR_5$, —$COR_6$ and —COOH are bonded to different C atoms and if $Z_3$ is a cyclic radical and m and/or n are 2, the —COR$_5$ or —COOH group is in the orthoposition to the —COR$_6$ group or to the adjoining carboxamide group, after which the reaction product may or may not be cyclised to the corresponding imide.

8. A compound according to claim 2 in which a is an integer from 1 to 15.

9. A compound according to claim 2 in which Y$_1$ and Y$_2$ are each a

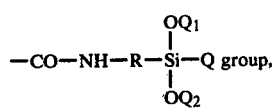

group,

R is $-(CH_2)_{\overline{a}}$ or 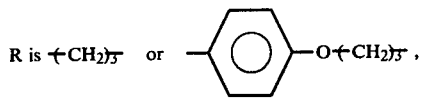

Q is methyl or alkoxy with 1–4 C atoms and Q$_1$ and Q$_2$ are each alkyl with 1–4 C atoms.

10. A compound according to claim 1 wherein A is —CH=CH—.

11. A compound according to claim 1 wherein a is an integer from 1 to 10.

12. An adhesion promoter for improving adhesion between an inorganic substrate and organic poymer which comprises a compound according to claim 1 wherein a is an integer from 1 to 15.

13. A shaped article which comprises a compound according to claim 1 wherein a is an integer from 15 to 50.

* * * * *